US007832655B2

(12) United States Patent
Tollens et al.

(10) Patent No.: US 7,832,655 B2
(45) Date of Patent: Nov. 16, 2010

(54) DELIVERY SYSTEM FOR GENERATING LIQUID ACTIVE MATERIALS USING AN ELECTROMECHANICAL TRANSDUCER

(75) Inventors: Fernando Ray Tollens, Cincinnati, OH (US); Steven Louis Diersing, Cincinnati, OH (US); John Philip Hecht, West Chester, OH (US); Steven James Schroeck, Cincinnati, OH (US); William Paul Mahoney, III, Liberty, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 11/903,315

(22) Filed: Sep. 21, 2007

(65) Prior Publication Data

US 2008/0073443 A1 Mar. 27, 2008

Related U.S. Application Data

(60) Provisional application No. 60/846,598, filed on Sep. 22, 2006.

(51) Int. Cl.
*B05B 17/04* (2006.01)

(52) U.S. Cl. ............................... 239/4; 239/69; 239/70; 239/102.2; 239/552; 239/556; 239/601; 222/638; 222/639

(58) Field of Classification Search ..................... 239/4, 239/67, 69, 70, 102.1, 102.2, 548, 552, 556, 239/558, 596, 601; 222/638, 639, 649; 423/123
See application file for complete search history.

(56) References Cited

U.S. PATENT DOCUMENTS

| | | | |
|---|---|---|---|
| 3,543,122 A | 11/1970 | Klebanoff et al. | |
| 3,615,041 A | 10/1971 | Bischoff | |
| 4,479,609 A | 10/1984 | Maeda et al. | |
| 4,533,082 A | 8/1985 | Maehara et al. | |
| 4,790,479 A | 12/1988 | Matsumoto et al. | |
| 5,297,734 A | 3/1994 | Toda | |
| 5,518,179 A | 5/1996 | Humberstone et al. | |
| 6,293,474 B1 | 9/2001 | Helf et al. | |
| 6,341,732 B1 | 1/2002 | Martin et al. | |
| 6,378,780 B1 | 4/2002 | Martens, III et al. | |
| 6,386,462 B1 | 5/2002 | Martens, III | |
| 6,439,474 B2 * | 8/2002 | Denen | 239/102.2 |
| 6,857,580 B2 * | 2/2005 | Walter et al. | 239/102.2 |
| 6,969,008 B2 * | 11/2005 | Helf et al. | 239/4 |
| 7,455,245 B2 * | 11/2008 | Sipinski et al. | 239/70 |
| 7,622,073 B2 * | 11/2009 | Schramm et al. | 422/123 |

(Continued)

OTHER PUBLICATIONS

PCT International Search Report dated Apr. 4, 2008—4 pgs.

*Primary Examiner*—Steven J Ganey
(74) *Attorney, Agent, or Firm*—Amy I Ahn-Roll; Leonard W Lewis

(57) ABSTRACT

A delivery system and methods for generating droplets of liquid active materials, such as a perfume, air freshener, insecticide formulation, and volatile materials, to the atmosphere by means of a electromechanical transducer. The electromechanical transducer employs a first period of activation and a second period of deactivation to increase the distribution of volatile materials contained within the liquid active materials to the atmosphere and reduce the hedonic habituation of the user. The electromechanical transducer is configured to improve flow rate and decrease deposition of the droplets on to nearby surfaces.

20 Claims, 3 Drawing Sheets

U.S. PATENT DOCUMENTS

2003/0102384 A1 6/2003 Walter et al.
2006/0011737 A1 1/2006 Amenos et al.
2006/0175426 A1 8/2006 Schramm et al.

* cited by examiner

DELIVERY SYSTEM FOR GENERATING LIQUID ACTIVE MATERIALS USING AN ELECTROMECHANICAL TRANSDUCER

CROSS REFERENCE TO RELATED APPLICATION

This application claims the benefit of U.S. Provisional Application No. 60/846,598, filed Sep. 22, 2006.

FIELD OF THE INVENTION

The present invention relates to a delivery system for generating liquid active materials, such as perfumes, air fresheners, insecticide formulations, and volatile materials, to the atmosphere by means of an electromechanical transducer.

BACKGROUND OF THE INVENTION

A number of processes exist for the generation of liquid droplets using electromechanical actuation. One method for such distribution is to atomize a liquid by a delivery system comprising a perforate structure which is vibrated by an electromechanical transducer which has a composite thin-walled or planar structure, and is arranged to operate in a bending mode. Liquid is supplied to the vibrating perforate structure and sprayed therefrom in droplets upon vibration of the perforate structure. Such attempts in the art are illustrated in U.S. Pat. Nos. 3,543,122, 3,615,041, 4,479,609, 4,533,082, 4,790, 479, 5,518,179, 5,297,734, 6,341,732, 6,378,780, and 6,386, 462.

While electromechanical transducer delivery systems are known in art, their difficulties are known as well. Specifically, there have been efforts to improve the overall distribution of the atomized liquids in a volume of space. However, many of these delivery systems suffer because of their inability to properly “loft” the atomized liquids in the air high enough to achieve sufficient dispersion such that the distribution of the liquid active materials is maximized. Thus, a need exists for an improved delivery system and method for generating droplets of liquid active materials to increase the distribution of the liquid active materials beyond that which is currently capable.

SUMMARY OF THE INVENTION

The invention relates to a delivery system for generating droplets of liquid active materials such as perfumes, other volatile liquids and/or volatile materials including a liquid supply component comprising a liquid reservoir containing a liquid; an electromechanical transducer upon excitation by a power supply; a droplet generation element operatively associated with the electromechanical transducer and positioned for contact with the liquid; and a timing mechanism for activating said electromechanical transducer over a first period, and deactivating said electromechanical transducer over a second period; wherein said first period is between about 20 and about 120 milliseconds.

The invention also relates to a method of distributing liquid active materials to an atmosphere comprising the steps of: providing a quantity of the liquid active materials; providing an electromechanical transducer in communication with the liquid active material; activating the electromechanical transducer to distribute the liquid active material to the atmosphere; and carrying out the activation for a first period of time of at least about 20 milliseconds.

The invention also relates to a method of distributing liquid active materials to an atmosphere comprising the steps of: providing a quantity of said liquid active materials; providing an electromechanical transducer in communication with said liquid active materials; activating said electromechanical transducer for a first period; deactivating the transducer for a second period, said first period and second period forming a operating cycle and repeating said operating cycle at least once, wherein said first period is at least about 20 milliseconds.

BRIEF DESCRIPTION OF THE DRAWINGS

While the specification concludes with the claims particularly pointing and distinctly claiming the invention, it is believed that the present invention will be better understood from the following description taken in conjunction with the accompanying drawings in which:

DETAILED DESCRIPTION OF THE INVENTION

Figure 1:
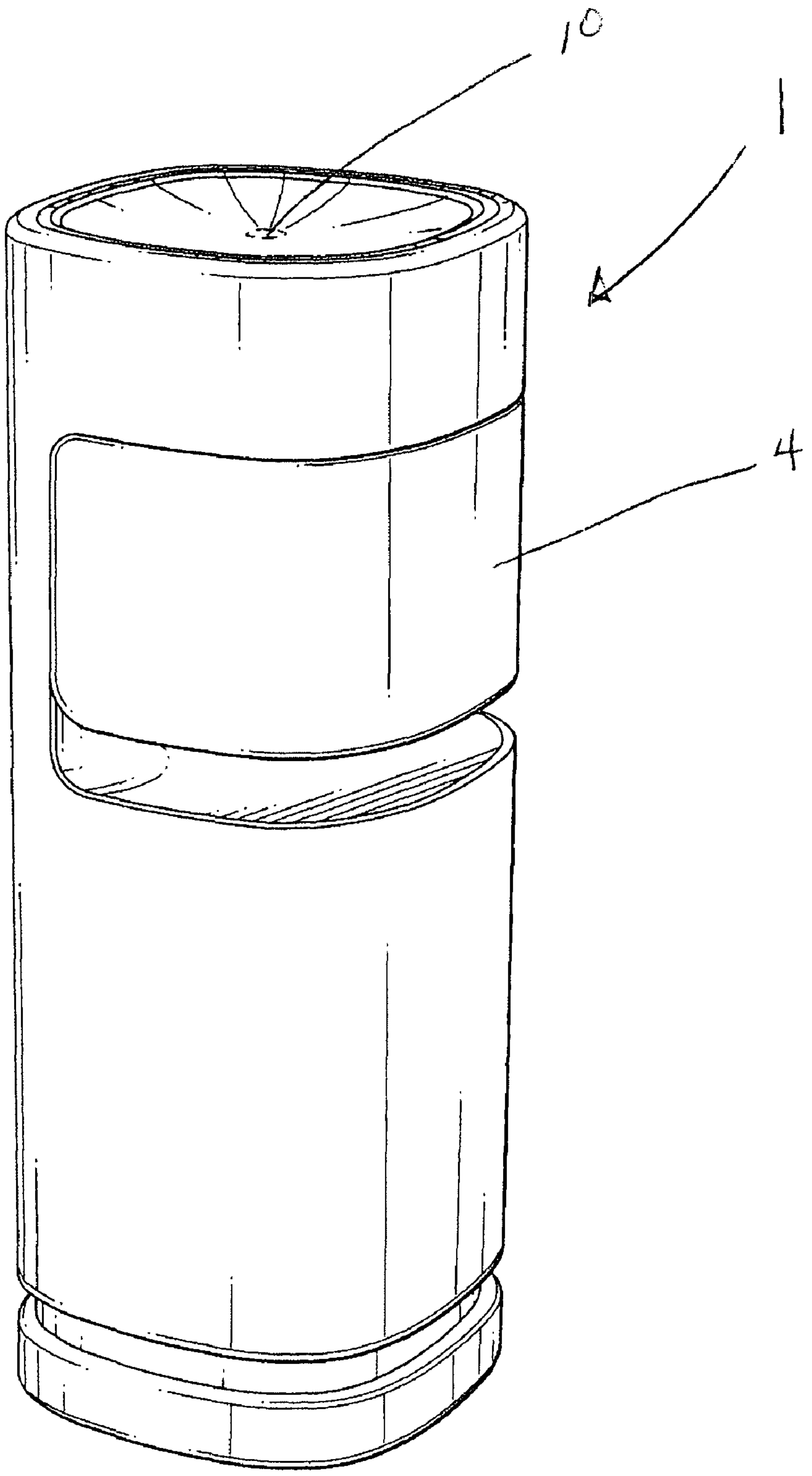
FIG. 1 is a perspective view of one embodiment of a delivery system of the present invention.

The present invention relates to a delivery system and methods described above. Without wishing to be bound by theory, it is believed that controlling the length of the first period and the second period provides a surprising increase in the distribution of the volatile materials contained within the liquid active materials and reduction of the hedonic habituation of the user. By controlling the length of the first period of time and the second period of time, the transition or evaporation of liquid droplets to finer droplets and/or a gaseous state as a means to increase liquid active material distribution is improved. The length of the first period controls the increased evaporation rate of the droplets of the liquid active materials, enhancing their transition to an atomized or molecular state and increasing their ability to remain airborne, disperse, and diffuse. In turn, this increases the room fill capability of the liquid active materials. The second period or the deactivation period, in one aspect, is used to reduce the level of habituation by the user. Habituation is a process used by the olfactory sensory system to reduce its sensitivity to a previously detected scent. Without wishing to be bound by theory, the second period of time allows for the volatile concentration of the liquid active materials to reduce below the habituation level threshold allowing the reset of the olfactory system and the re-detection or re-perception of the scent. In effect, the first and second periods surprisingly increase the perceived intensity of the liquid active formulation.

Timing Mechanism

Controlling the length of the first period and second period according to the present invention creates chimney or “air-bus” effect wherein the amount of air entrainment as well as the velocity of the droplets increase, resulting in an increased concentration of airborne volatile materials from the liquid active materials as evidence by the higher detection of components. This effect improves the perceived intensity and hedonics of the liquid active material. The timing mechanism can be controlled by any of the known intelligent systems in the art. The first period and second period, together forming an operating cycle, can be repeated at least once. In another embodiment, the operating cycle is repeated until the liquid active material is exhausted and/or the power supply is exhausted.

In one embodiment, the first period is at least about 5 milliseconds; in another embodiment at least about 10 milliseconds; in another embodiment at least about 20 milliseconds; in another embodiment at least about 50 milliseconds; in another embodiment at least about 100 milliseconds; in another embodiment at least about 250 milliseconds; in another embodiment at least about 500 milliseconds; in another embodiment at least about 1 second; in another embodiment at least about 5 seconds. In another embodiment, the first period is between about 5 milliseconds and about 5 seconds; in another embodiment between about 10 milliseconds and 1 second; in another embodiment between about 20 milliseconds and 500 milliseconds; in another embodiment between about 50 milliseconds and 100 milliseconds.

In one embodiment, the second period is between about 1 second and 30 hours; in another embodiment between about 1 second and 24 hours; in another embodiment between about 5 seconds and 12 hours; in another embodiment between about 5 seconds and 8 hours; in another embodiment between about 5 seconds and 6 hours; in another embodiment between about 5 seconds and 4 hours; in another embodiment between about 5 seconds and 3 hours; in another embodiment between about 5 seconds and about 2 hours; in another embodiment between about 5 seconds and about 1 hour; in another embodiment between about 5 seconds and 45 minutes; in another embodiment between about 5 seconds and 30 minutes; in another embodiment between about 5 seconds and 20 minutes; in another embodiment between about 5 seconds and 15 minutes; in another embodiment between about 5 seconds and 10 minutes; in another embodiment between about 5 seconds and about 5 minutes; in another embodiment between about 5 seconds and about 150 seconds; in another embodiment between about 20 seconds and about 120 seconds; in another embodiment between about 25 seconds and about 80 seconds; in another embodiment between about 10 seconds and about 40 seconds. It is understood, however, that periods of time longer than the above ranges of time may be utilized with the present invention.

Liquid Active Materials

The liquid active materials of the present invention include volatile materials, nonvolatile materials, and combinations thereof. The liquid active materials of the present invention readily flow at temperatures of between about 10° C. and about 30° C. The liquid active materials may be generated in various facilities, which include but are not limited to rooms, houses, hospitals, offices, theaters, buildings, and the like, or into various vehicles such as trains, subways, automobiles, airplanes, the outdoors and the like. The volatile materials of interest herein can be in any suitable form including, but not limited to: dispersion of solids, emulsions, liquids, and combinations thereof. For example, the delivery system may contain a volatile material comprising a single-phase composition, multi-phase composition and combinations thereof, from one or more sources in one or more carrier materials (e.g. water, solvent, etc.).

Nonvolatile materials, including solids, are also contemplated for use with the present invention. It is believed that when nonvolatile materials are part of the liquid active material, the nonvolatile materials are finely dispersed in the air into particles capable of being at least partially carried by air.

It should be understood that when the droplets of liquid active materials are described herein as being "distributed", "generated" or "released", this refers to the volatilization of the evaporative components of the volatile materials and to the release to the atmosphere of the non-evaporative components, which may be small solids or particulates.

The term "solids" as used herein, refers to a material that has a tangible or concrete form as discrete material at room temperature (22° C.), that is, they tend to keep their form rather than flow or spread out like liquids or gases. The solids may be dissolved in the formulation or suspended throughout. Solids may behave very similar to base notes as they bring depth and body to a perfume. The terms "volatile materials", "aroma", and "scents", as used herein, include, but are not limited to pleasant or savory smells, and, thus, also encompass scents that function as fragrances, deodorizers, odor eliminators, malodor counteractants, insecticides, insect repellants, medicinal substances, air fresheners, deodorants, aromacology, aromatherapy, or any other odor that acts to condition, modify, or otherwise charge the atmosphere or to modify the atmosphere.

In addition, the term "volatile materials" as used herein, refers to a material or a discrete unit comprised of one or more materials that is vaporizable, or comprises a material that is vaporizable without the need of an energy source. Any suitable volatile material in any amount or form may be used. The term "volatile materials" includes but is not limited to compositions that are comprised entirely of a single volatile material. It should be understood that the term "volatile material" also refers to compositions that have more than one volatile component, and it is not necessary for all of the component materials of the volatile material to be volatile. The volatile materials described herein may, thus, also have non-volatile components.

The volatile material may comprise a perfume, although the invention is not so limited. A perfume may include a single aromatic chemical or a mixture of aromatic chemicals. As used herein, aromatic chemicals mean chemicals that have an odor. There are several chemical classes which fall within aromatic chemicals, including but not limited to ionones, hydrocarbons, alcohols, aldehydes, ketones, esters, etc.

The term "fragrance" or "perfume" refers to all organic substances which have a desired olfactory property and are essentially nontoxic. They can be compounds of natural, semi synthetic or synthetic origin. A fragrance can be a combination of various odorous substances which evaporate at different rates and/or during different periods. Fragrance can exhibit what is known as a "top note," which may be the odor which first diffuses when the fragrance is applied, generated or released to the atmosphere, a "heart note" or "middle note," which may complete or complement the fragrance providing body and texture, and a "base note," which may be the most substantive odor and can be perceived several hours after application or emission.

In order to be noticeable, a perfume has to be volatile, its molecular weight being an important factor along with the nature of the functional groups and the structure of the chemical compound. Thus, most perfumes have molecular weights of up to about 200 Dalton, with molecular weights of 300 Dalton and higher being more the exception. In view of the differences in volatility of perfumes, the odor of a perfume or fragrance composed of several perfumes changes during the evaporation process, the odor impressions being divided into the top note, the middle note or body and the base note.

Since odor perception is also based to a large extent on odor intensity, the top note of a perfume or fragrance may not consist solely of readily volatile compounds. The base note may consist largely of less volatile, i.e. firmly adhering, perfumes. In the composition of perfumes, more readily volatile perfumes may be fixed, for example, to certain "fixatives", which prevents them from vaporizing too rapidly. The perfume may also contain small amounts of other additives, such as solvents, preservatives, antioxidants, UV screening agents and the like. The fragrance matrix may also include organoleptic components, such as for example, other well-known fragrance ingredients. The fragrances or perfumes may include natural and/or synthetic oils, extracts and/or essences which may comprise complex mixtures of constituents, such as orange oil, lemon oil, rose extract, lavender, musk, patchouli, balsam essence, sandalwood oil, pine oil, and cedar oil.

A useful term to quantify the degree of volatility of the volatile materials is the Kovat's Index. The Kovat's Index (KI, or Retention Index) may be defined by the selective retention of solutes or perfume raw materials (PRMs) onto the chromatographic columns. It is primarily determined by the column stationary phase and the properties of solutes or PRMs. For a given column system, a PRM's polarity, molecular weight, vapor pressure, boiling point and the stationary phase property determine the extent of retention. To systematically express the retention of analyte on a given GC column, a measure called Kovat's Index is defined. The Kovat's Index places the volatility attributes of an analyte (or PRM) on a column in relation to the volatility characteristics of n-alkane series on that column. Typical columns used are DB-5 and DB-1.

By this definition the KI of a normal alkane may be set to 100n, where n=number of C atoms of the n-alkane. With this definition, the Kovat's index of a PRM, x, eluting at time t', between two n-alkanes with number of carbon atoms n and N having corrected retention times t'n and t'N respectively will then be calculated as:

$$KI = 100\times\left(n + \frac{\log t'_x - \log t'_n}{\log t'_N - \log t'_n}\right) \quad (1)$$

This equation can be used to calculate the Kovat's index for any volatile material. Furthermore, this equation can be used to further separate volatile components into three categories; top, middle and base notes. Using the Kovat's index, a top note may as have a KI less than or equal to 1200, a middle note between 1200 and 1400, and a base note greater than or equal to 1400. For example, a typical perfume formulation having 2 percent solids may comprise 70 percent top notes, 20 percent middle notes, and 10 percent bottom notes. A, comparable formulation having about 3 percent solids may comprise about 40 to about 60 percent, particularly about 50 percent top notes; about 20 to about 40 percent, particularly about 30 percent middle notes; and about 10 to about 30 percent, particularly about 20 percent bottom notes.

Delivery System

Figure 2:
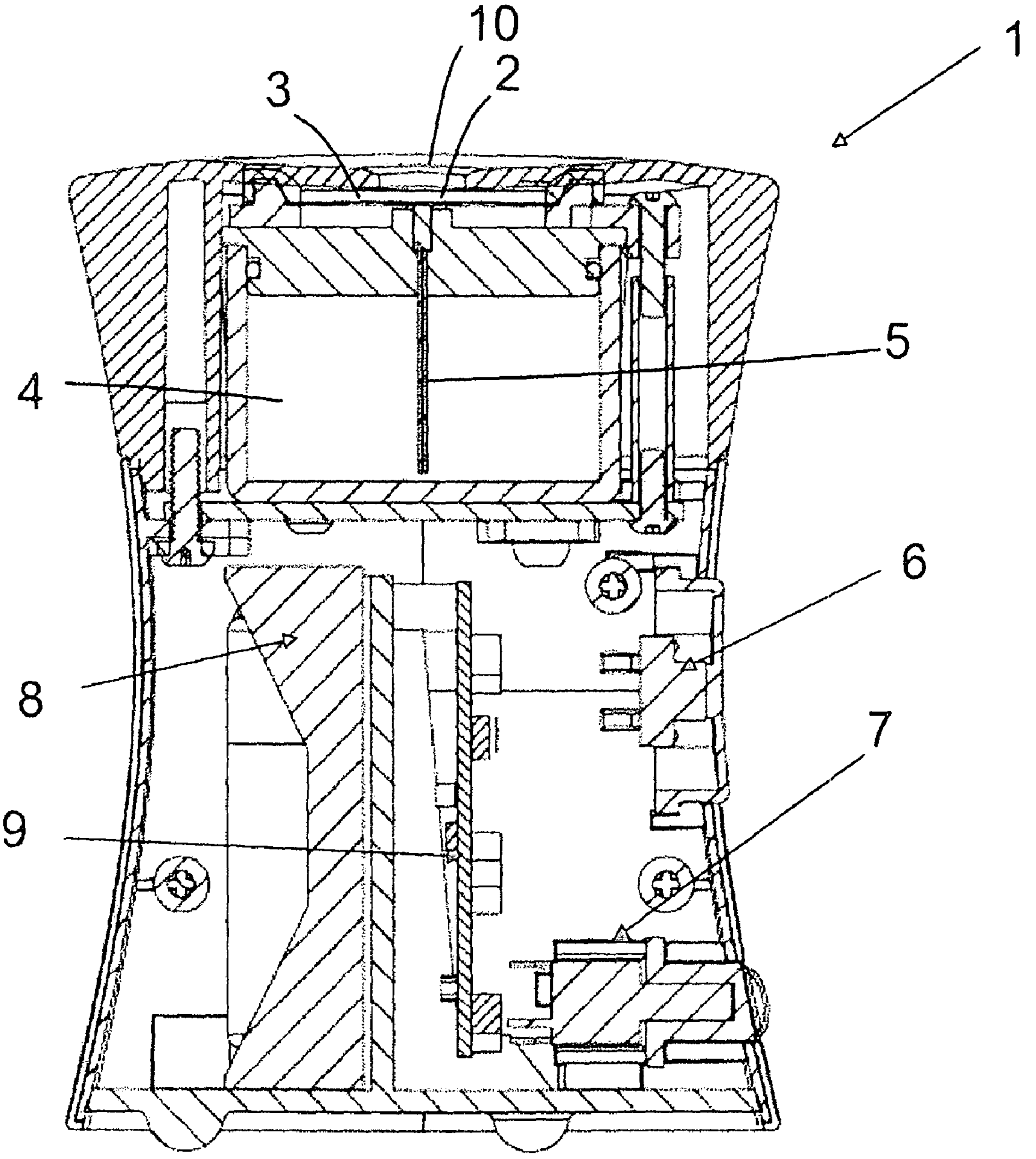
FIG. 2 is a cross-sectional view of one embodiment of a delivery system of the present invention.

Now referring to FIGS. 1 and 2, a non-limiting and exemplary delivery system 1 is shown. The delivery system 1 includes a liquid reservoir 4, which contains a liquid active material to be atomized, that may be juxtaposed with and mounted below the electromechanical transducer 3 and droplet generation element 2. The liquid supply component 5 may extend upwardly from within the reservoir 4 to the rear face of the droplet generation element 2 or to a region in fluid communication with the droplet generation element 2. Upon activation of the electromechanical transducer 3, the liquid active material is generated through the droplet generation element 2, the orifice 10, and into the atmosphere.

The reservoir 4 may comprise any liquid tight container suitable for holding an adequate quantity of the liquid active materials to be dispensed. The reservoir 4 may be pressurized to provide for delivery of the liquid active materials to the droplet generation element 2, or may be maintained at atmospheric pressure. Upon depletion of the reservoir 4, the reservoir 4 may be refillable with liquid active material provided from a bulk supply or the reservoir 4 may be replaced with a new reservoir containing a quantity of liquid active material.

The liquid active materials may be delivered to a droplet generation element 2 by a liquid supply component 5 working by gravity feed, capillary action, pumping action, etc. When the droplet generation element 2 is a perforate structure, the liquid supply component 5 may be disposed near the center of the droplet generation element 2 so that the liquid supply component 5 may contact the perforations 2*a*, 2*b*, 2*c* of the droplet generation element 8. However, the liquid supply component 5 need not contact the perforations 2*a*, 2*b*, 2*c* and the perforations 2*a*, 2*b*, 2*c* may be laterally displaced from the liquid supply component 5.

A continuous feed of the liquid active material from the reservoir 4 to the droplet generation element 2 may be desired. The continuous feed may be accomplished by a using liquid supply component 5, which may comprise a feed tube that delivers liquid active material to the rear face of the droplet generation element 2 or to a position juxtaposed with the rear face of the droplet generation element 2. The rear face of the droplet generation element 2 is the face opposite from which the droplets emerge. The liquid active materials may be delivered from the reservoir 4 to one face of the droplet generation element 2 by a capillary feed. The capillary feed may be flexible and have a surface or assembly of surfaces over which liquid active material can pass from the reservoir 4 towards the droplet generation element 2. Exemplary capillary material forms include open cell foams, fibrous wicks, porous plastic wicks, and glass or polymeric capillary tubes.

In applications where relatively high droplet production rates and/or a relatively high percentage of solid are desired, capillary feed may be provided by a relatively open structure, which may also be relatively rigid. This arrangement may provide the advantage of a relatively large, unrestricted area for liquid flow for a given surface area at the wall of the capillary tube. In such a liquid transfer process the area between the capillary material surfaces through which liquid may flow to the capillary surfaces, i.e., liquid volume is relatively large to the surface area of the capillary surfaces. This geometry may provide a liquid transfer process which is less restrictive than a similar transfer process utilizing a porous capillary wick. Without being bound by theory, it is believed that an open tube capillary may minimize the interaction between the capillary system porous media and the dispersed solids, thereby allowing the solids to be generated with the droplets as part of the bulk liquid with minimal liquid to solid separation. The open capillary tube may have a delivery rate of at least about 20, about 30 or about 40 mg/hr, but is typically not more than about 80, about 70, about 60 or about 50 mg/hr.

The capillary tube may have a closed cross section, such as a circle. Alternatively, the closed cross section may be non-circular, such as an oval, square, etc. Alternatively, the open capillary tube may comprise an open channel, such as a weir, etc. The capillary tube may be rigid and made of glass, polymeric materials, etc.

Furthermore, in applications where the droplet production rates in the range of 1 mg/s or more are desired, flat channel capillaries may offer the benefit of a relatively greater delivery rate with a simple design and ease of manufacturing. When using a flat channel design consideration may be given to the height of the capillary, since the drag pull on a flat capillary channel is half of that of a capillary tube, resulting in only half of the capillary rise compared to a closed tube.

If desired, plural capillary tubes may be used in parallel to transport liquid from the reservoir to the actuator. If plural capillary tubes are used, the capillary tubes may be of equal or unequal length, cross-sectional area, cross-sectional shape, length, delivery rate, etc. The capillary tubes may have a common or different origin within the reservoir. Alternatively, plural capillary tubes may be utilized to deliver a like number of plural liquids from separate reservoirs to a common perforate structure. This arrangement provides the advantage that incompatible materials may be kept apart, in discrete reservoirs, until these materials are dispensed at the point of use. The plural materials may be fed from their respective reservoirs to the perforate structure at the same flow rate or at different flow rates.

In yet another alternative embodiment having plural reservoirs, plural transducers and a like number of plural perforate structures may be utilized and operated in parallel. This arrangement provides the advantage that no mixing of separate materials occurs until the materials are dispensed into the atmosphere. Again, the materials may be dispensed at a common flow rate or at different flow rates. If so the plural reservoirs, transducers, perforate plates, etc. may be the same or may differ in function and/or performance.

The delivery system 1 may comprise an electromechanical transducer 3, which is an element capable of converting electrical energy to mechanical energy. One known example of an electromechanical transducer 3 comprises piezoelectric materials, which have the ability to change shape when subject to an externally applied voltage. The voltage may cause the electromechanical transducer 3 to vibrate at certain frequencies. The electromechanical transducer 3 may be driven with an oscillating voltage at one of the resonant frequencies of the system or alternatively with a waveform that gives droplet on demand operation. The oscillating voltage may produce a vibration in the transducer. The vibration may, in turn, generate[s] droplets of liquid active material through a droplet generation element 2, such as a perforate structure that is operatively associated with the electromechanical transducer 3. The droplets of liquid active material are then distributed to the atmosphere. It is believed that a resultant pressure differential may be induced in the liquid directly behind a perforate structure. The resulting pressure differential may force the liquid through the perforations of a perforate structure to form droplets.

The electromechanical transducer 3 may comprise a piezoelectric material, which vibrates at a resonant frequency under an externally applied voltage. The electromechanical transducer 3 may comprise various shapes and forms, such as a round disc. A disc-shaped transducer may have two opposed faces. A separate electrode may be disposed on each face and be radially poled. The electrodes may excite the length modes of the disc shaped transducer or a mode of a perforate structure.

The electrodes may be patterned so as to incorporate "drive" and "sense" electrodes. The drive and sense electrodes are electrically insulated but mechanically coupled through the piezoelectric transducer. A drive voltage may be applied to the drive electrode. The resulting motion in the transducer generates a voltage at the sense electrode. This voltage can then be monitored and used to control the drive voltage through a feedback circuit. The electrical response may be used to adjust the voltage to achieve specified resonances either by phase locking, amplitude maximizing or other known means. In order to maximize the electromechanical coupling to the desired mode it may be useful to shape the drive electrode appropriately.

The induced vibration may have an amplitude and phase induced in relation to characteristics of the drive signal. If desired, the drive voltage may sweep various frequencies, to provide a range of dispensing characteristics. Alternatively, the drive voltage may excite the transducer at a single frequency. The single frequency may be coincident or near the transducer's natural frequency or a harmonic thereof. This arrangement may provide the benefit that less power is consumed than using a sweep of multiple frequencies over a spectrum.

In may also be useful to incorporate a sense electrode into the delivery system 1. A sense electrode can give phase and amplitude information that allows an appropriate electronic circuit to lock on to the correct resonant mode. It may be advantageous to shape the sense electrode so as to achieve appropriate electromechanical coupling.

Figure 3:
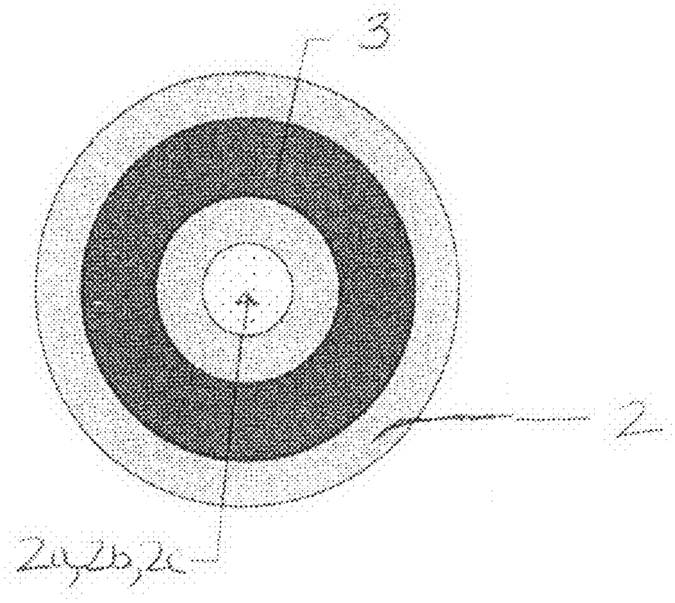
FIG. 3 is an enlarged top view of one embodiment of the droplet generation element of the present invention.
Figure 4:
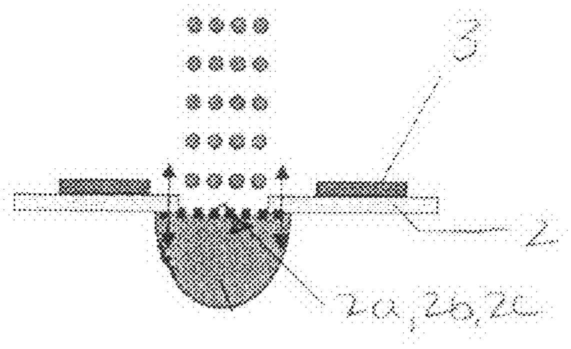
FIG. 4 is an enlarged cross-sectional view of the droplet generation element in FIG. 3.

One embodiment of the electromechanical transducer 3 is shown in FIGS. 3 and 4. In this embodiment, the electromechanical transducer 3 can have a diameter of about 10 to about 50 millimeters. In certain embodiments the diameter may be less than about 25 millimeters, less than about 20 millimeters, or may be 15 about millimeters or less. The electromechanical transducer 3 may have a centrally located aperture therethrough. The aperture may have a diameter of about 5 millimeters to about 15 millimeters. The electromechanical transducer 3 may be flat and vibrate in a bending mode, expanding mode or combination thereof with a major excursion generally perpendicular to the opposed faces of the transducer. The bending may be bilateral or unilateral. A suitable piezoelectric transducer is disclosed in U.S. Pat. No. 5,518,179, the disclosure of which is incorporated by reference.

The droplet generation element 2 may be formed from a variety of materials including electro formed nickel, etched silicon, stainless steel or plastics. The droplet generation element 2 may be flexible or stiff. A flexible design is one where the amplitudes of the vibrational modes of the droplet generation element 2 are large compared with those of the electromechanical transducer 3. The resulting motion may have a significant effect on the droplet generation process. A stiff design is one where the amplitudes of the vibrational modes of the perforate structure are generally equal to or smaller than those of the electromechanical transducer. This motion generally follows the motion of the electromechanical transducer. In either design, the flexibility may be controlled by a choice of material and thickness. The benefit of the stiff design is that a stiff droplet generation element may generate uniform droplets across its surface without dampening the overall motion of the droplet generation element.

The droplet generation element 2 is operatively associated with the electromechanical transducer 3. "Operatively associated" means that the droplet generation element is responsive to the activation of the electromechanical transducer 3 such that the liquid active material passes through the droplet generation element 2 for diffusion into the atmosphere. In one embodiment, the droplet generation element 2 is operatively associated with the electromechanical transducer 3 by being joined or coupled to one face of the electromechanical transducer 3 by adhesive, solder, etc. A non-limiting, exemplary coupled electromechanical transducer 3 is shown in FIG. 4. The droplet generation element 2 may also be de-coupled from the electromechanical transducer 3, yet still be operatively associated with the transducer 3. A suitable de-coupled electromechanical transducer is described in WO 02/068128, which is incorporated in its entirety herein.

The droplet generation element 2 may be a perforate structure, as shown in FIGS. 3 and 4, that comprises plural perforations 2*a*, 2*b*, 2*c* disposed on a pattern, such as a hexagonal lattice. It has been found that structuring the droplet generation element to maximize the flow rate of the liquid active material while minimizing deposition enhances the perceived intensity of the liquid active formulation.

The droplet size may be determined by varying the cross sectional area of the exit of the perforations 2*a*, 2*b*, 2*c*. Round perforations 2*a*, 2*b*, 2*c* may have a diameter of about 1 to about 100 microns. In one embodiment, the diameter of the perforations 2_a_, 2_b_, 2_c_ may be less than about 30 microns. In another embodiment, the diameter of the perforations 2_a_, 2_b_, 2_c_ may be less than about 15 microns. Alternatively, the diameter of the perforations 2_a_, 2_b_, 2_c_ may be between about 2 to about 10 microns. Alternatively, the diameter of the perforations 2_a_, 2_b_, 2_c_ may be between about 4 to about 8 microns. Alternatively, the diameter of the perforations 2_a_, 2_b_, 2_c_ may be between about 5 to about 7 microns.

The perforations 2_a_, 2_b_, 2_c_ may be tapered to have a reduction in cross-sectional area in the flow direction. If a perforate structure having perforations 2_a_, 2_b_, 2_c_ of variable cross section is selected, the cross sectional area of the perforations 2_a_, 2_b_, 2_c_ may decrease from the rear face to the front face of the perforate structure. Such a tapered perforation may reduce the amplitude of vibration of the perforate structure which is necessary in order to produce droplets of a given size, due to the reduction of viscous drag upon the liquid as it passes through such perforations 2_a_, 2_b_, 2_c_. Consequently, a relatively lower excitation of the electromechanical transducer 3 may be used, thereby providing improved efficiency in creating the droplets to be dispensed. In the case of a coupled electromechanical transducer and perforate structure, the relatively lesser excitation may enable the use of a relatively thick and robust perforate structure from which satisfactory droplet production can be achieved. This may also provide the successful creation of droplets from liquids of relatively high viscosity and may reduce the mechanical stresses in the perforate structure. In the case of a decoupled electromechanical transducer and perforate structure, the reduction of viscous drag will also result in improved efficiency with respect to the power that is necessary to generate the droplets.

The droplet generation element 2 may also be a non-perforate structure. For example, the liquid active material is fed onto a face of the droplet generation element 2 that is opposite the rear face. Droplets are generated by vibration of the droplet generation element 2 whether it is bending, expanding, bilateral or unilateral.

The delivery system 1 may have a first, disposable part, comprising the liquid and its container or liquid reservoir 4. The second part, may be reusable, and may comprise the electromechanical transducer 3, the droplet generation element 2 with its associated drive electronics 9 and a power supply 8. This provides a system which is refillable. Alternatively, the system may be discarded upon depletion of the reservoir.

The delivery system can be operated from any suitable power supply 8. The power supply 8 may be a battery, electrical power from a wall outlet, solar photovoltaic conversion, etc.

The delivery system may further comprise an automatic switch, as is known in the art. The automatic switch may activate or deactivate the delivery system when a threshold amount of energy is or is not present. For example, the automatic switch may comprise a photocell. The photocell may cause the delivery system to shut down, when a threshold amount of light is not present. This allows the delivery system to shut down at night, in case people are not present during the evening. The photocell may shut down the either the fan, electromechanical transducer, or both. Alternatively, the delivery system, transducer and/or fan may be activated by, or be rendered inactive by, the presence or absence of sound, motion, heat or other energy forms.

The delivery system 1 may further comprise an intensity controller 9 for controlling the amount of liquid active material that is dispensed into the atmosphere. The delivery system 1 may also include a boost controller 8 for providing bursts of liquid active material beyond the amount normally dispensed from the delivery system 1. In another embodiment a heater may be utilized to assist in and accelerate the volatilization of the liquid active materials.

The delivery system 1 may further comprise a light source. Suitable light sources include but are not limited to light generating diodes ("LEDs"), incandescent sources of light including but not limited to filament-based bulbs, and luminescent sources of light including but not limited to electroluminescent, chemiluminescent, cathodoluminescent, triboluminescent, and photoluminscent materials. In one non-limiting embodiment the light source is one or more LEDs. The LED can be any number of colors including but not limited to yellow, white, red, green, blue, pink, or a combination thereof. One non-limiting example of an LED suitable for use with the present invention is part No. MV8305 (available from Fairchild Semiconductor of South Portland, Me.).

In one non-limiting embodiment, the light is positioned on the delivery system 1 such the light is directed towards the reservoir 4. It may be designed such that the light turns on automatically when the delivery system 1 is turned on or designed such that the light is controlled separately from the operation of the delivery system 1. If desired, the light source could be connected to a timer incorporated in the delivery system 1 such that the light automatically turns-off after a predetermined time period. Also, if desired, the light source may provide a light that is varying in intensity.

The following examples are presented for illustrative purposes, and are not intended, in any way, to limit the scope of the invention.

EXAMPLE 1

Example 1 compares the effect of the length of activation period on perceived intensity using a piezoelectric delivery system according to the following Sensory Evaluation Method for delivery systems or apparatus.

A dedicated odor evaluation room is utilized for all sensory evaluations. A trained odor evaluator verifies that there is not any residual perfume or room odor present in the room. The door(s) to the room are closed and the delivery system or apparatus is activated by a test facilitator. Trained odor evaluators enter the odor evaluation room and perform odor evaluations at the following time intervals: (1) 3 minutes after activation (2) 6 minutes after activation (3) 12 minutes after activation and (4) 18 minutes after activation. The sensory evaluations are conducted at the following distances from the delivery system or apparatus starting at the furthest distance: (1) 0.9 meters (2) 1.8 meters and (3) 2.7 meters. Expert evaluators exit the room between odor evaluations and the door(s) are closed between odor evaluations. Expert evaluators provide odor intensity measurements on a sensory rating scale of 0-5.

Perfume Intensity Scale:

5=very strong, i.e., extremely overpowering, permeates into nose, can almost taste it 4=strong, i.e., very room filling, but slightly overpowering 3=moderate, i.e., room filling, odor character clearly recognizable 2=light, i.e., fills part of the room, with recognizable odor character 1=weak, i.e., diffusion is limited, odor character difficult to describe, 0=no scent Table 1 illustrates the improved perfume hedonic data at all distances from the delivery system when the length of the activation time of the electromechanical transducer is increased at constant delivering rate. This translates to the consumer as better perfume intensity and character.

TABLE 1

| | Perfume intensity grade at given distance from the delivery system | | |
|---|---|---|---|
| | 0.9 meters | 1.8 meters | 2.7 meters |
| Short Pulse (10 ms) | 1.5 | 0.5 | 0.5 |
| Medium Pulse (15 ms) | 2.0 | 1.5 | 1.5 |
| Longer Pulse (60 ms) | 2.5 | 2.5 | 2.0 |

A longer of activation period may deliver a higher intensity, more complex perfume character and a more substantive perfume presentation than a corresponding perfume using a shorter activation period.

EXAMPLE 2

Example 2 compares the effect of pulsation times with respect to the number of detectable components by the following method, in situ monitoring of perfume components by GC/MS.

In this method, the testing delivery system is placed in a 100 $ft^3$ room with standard room circulation. The samples are collected at 0.2, 3, 6, and 9 feet. For each time point a sample is taken at each position. An initial background room sample is taken. The delivery system is placed in the room and turned on. After that, samples are collected at initial, 6, 12 and 18 minutes. The air samples are collected using 4 Gil Air Personal Air Sampler pumps collecting samples for 3 minutes at 1 L/minute. Samples are collected on 50 mg Tenax TA traps and desorbed using an MPS-2 TDU into a GC/MS system. Samples are analyzed using a 6890/5973 GC/MS with a DB-1 column (1 μm film thickness, 0.32 mm ID, 60 m length). The data is reported with respect to the number of detectable components as well as Flame Ionization Detector response (FID).

Table 2 shows a higher number of detectable components at all measured distances from the delivery system at the 18 minute sample when longer pulsation time is used. Surprisingly, longer pulsation time produced significantly more detectable components even in the area directly beside the delivery system. Similar trends are observed at the other time measurements.

TABLE 2

| | Number of Detectable Components Given Distance from the Delivery system | | | |
|---|---|---|---|---|
| | 0.2 feet | 3 feet | 6 feet | 9 feet |
| Short Pulse (10 ms) | 7 | 7 | 6 | 7 |
| Long Pulse (60 ms) | 22 | 17 | 14 | 12 |

EXAMPLE 3

Example 3 compares the various perforation sizes of the droplet generation element and their effect on deposition and flow rate. To improve perceived intensity of the liquid active material, one may maximize flow rate while minimizing deposition. In this example, the delivery system provides deposition of less than about 6 μg and flow in the range of about 30 mg/hr and greater.

Flow rates are measured as weight loss over time. The weight of the delivery system is measured using a Mettler Toledo Excellence Xs403S response 0.001 g over time and the weight difference (in mg) was divided by the time period in hours to give a flow rate in mg/hr.

Plume height is determined by placing a delivery system into the center of a cylindrical chamber. At the rear of the chamber, behind the delivery system a darkened screen is provided. A ruler is positioned so that the zero cm mark is directly in line with the top of the delivery system. The vertical distance of the plume reached is measured by the ruler and the average plume height, in cm, is taken from five consecutive sprays.

Deposition of is determined by collecting the non-volatilized or re-deposited liquid active materials on three filter papers, Whatman 40 (Ashless, 18.5 cm Catalog number—1440 185). Two of filter papers are placed under the bottom edge of the delivery system. The third filter paper is cut to fit the top of the delivery system and placed with the hole cut out over the center of the delivery system. The delivery system is placed in a room and run for a period of 17 to 18 hours. Filter papers are extracted using 5 ml of a internal standard solvent solution containing 11.4 mg of C14 in 250 ml of methanol. All samples are analyzed by injecting 1 microliter onto a 6890/5973 CC/MS with a DB-1 column (1 μm film thickness, 0.32 mm ID, 60 m length). Quantitative results are calculated by referencing to a known standard.

Droplet-size distributions are measured using an Oxford Laser Visisizer System. This technique uses high-speed, high-resolution digital photography to acquire images of the spray. The laser light is diffused and used as a backlight (not a beam); the sample volume is approximately 1 mm3. These images are then analyzed by the Visisizer software to yield a droplet size distribution. The measured distributions appear rougher than distributions measured with other techniques (such as laser diffraction) since this method actually counts and sizes individual particles. Relevant spray statistics are then calculated from the raw droplet-size data. In most cases, at least 2000 droplets are used to calculate the statistics.

Table 3 illustrates that the a perforation size of about 5 microns to about 7 microns maximizes flow rate and minimizes deposition

TABLE 3

| Activation period (ms) | Deactivation period (ms) | Perforation Size (μm) | Droplet size (μm) | Plume height (cm) | Deposition (μg) | Flow Rate (mg/hr) |
|---|---|---|---|---|---|---|
| 15 | 10 | 4.5 | 6.5 | 7 | 6 | 10 |
| 45 | 10 | 8 | 11.80 | 10 | X | 42 |
| 60 | 2.5 | 4.5 | 7.40 | 8 | 3 | 35 |

TABLE 3-continued

| Activation period (ms) | Deactivation period (ms) | Perforation Size (μm) | Droplet size (μm) | Plume height (cm) | Deposition (μg) | Flow Rate (mg/hr) |
|---|---|---|---|---|---|---|
| 60 | 5 | 5.6 | 7.84 | 9 | 4 | 34 |
| 60 | 10 | 7 | 11.00 | 10 | 4 | 32 |
| 60 | 10 | 8 | 11.90 | 11 | 12 | 45 |
| 75 | 10 | 8 | 12.30 | 12.5 | 13 | 47 |
| 100 | 2.5 | 4.5 | 6.70 | 9.5 | 3 | 33 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A delivery system for generating droplets of liquid active material comprising:

a) a liquid reservoir, wherein the liquid reservoir contains a liquid active material;

b) an electromechanical transducer, said electromechanical transducer vibrates upon excitation by a power supply;

c) a droplet generation element operatively associated with said electromechanical transducer and positioned for contact with said liquid active material, said droplet generation element defines a plurality of perforations, said perforations having a diameter of about 5 microns to about 7 microns;

d) a timing mechanism for activating said electromechanical transducer over a first period, and alternatingly deactivating said electromechanical transducer over a second period;

wherein first period is between about 50 milliseconds and 120 milliseconds; and wherein the delivery system has a deposition rate of less than about 6 μg and a flow rate of about 30 mg/hr or greater.

2. A delivery system according to claim 1 wherein first period is between about 50 milliseconds and 100 milliseconds.

3. A delivery system according to claim 1 wherein first period is between about 60 milliseconds and 80 milliseconds.

4. A delivery system according to claim 1 wherein second period is between about 25 milliseconds and 80 milliseconds.

5. A delivery system according to claim 1 wherein second period is between about 10 milliseconds and 40 milliseconds.

6. A delivery system according to claim 1 wherein said timing mechanism substantially continuously activates said electromechanical transducer during said first time period.

7. A delivery system according to claim 1 wherein said timing mechanism substantially continuously deactivates said electromechanical transducer during said second time period.

8. A delivery system according to claim 1 wherein at least one of said first time period and said second time period can be adjusted by a user.

9. A delivery system according to claim 1 wherein at least one of said first time period can be activated on demand by the user.

10. A delivery system according to claim 1 wherein said electromechanical transducer is coupled to said droplet generation element.

11. A delivery system according to claim 1 wherein said electromechanical transducer is decoupled from said droplet generation element.

12. A delivery system according to claim 1 wherein said delivery system further comprises an orifice and wherein said delivery system generates said liquid active material into the atmosphere at about 8 cm from said orifice.

13. A method of distributing a liquid active material to an atmosphere, said method comprising the steps of:

(a) using a delivery system for generating droplets comprising:

a liquid reservoir, wherein the liquid reservoir contains a quantity of liquid active material, an electromechanical transducer in communication with said liquid active material, a droplet generation element operatively associated with said electromechanical transducer and positioned for contact with said liquid active material, said droplet generation element defines a plurality of perforations, said perforations having a diameter of about 5 microns to about 7 microns, wherein the delivery system has a deposition of less than about 6 μg and a flow rate of about 30 mg/hr or greater;

(b) activating said electromechanical transducer to distribute said liquid active material to said atmosphere; and (c) carrying out said activation for a first period of time of at least about 50 milliseconds.

14. A method according to claim 13 further comprising providing a quantity of a second liquid:

(a) using an electromechanical transducer in communication with said second liquid;

(b) activating said electromechanical transducer to distribute said second liquid to said atmosphere; and carrying out said activation for an alternate period of time of at least about 20 milliseconds.

15. A method according to claim 13 wherein said liquid active material is distributed to said atmosphere for said first period of time and said second liquid is distributed to said atmosphere for said alternate period, said first period and said alternate period being different.

16. A method according to claim 13 further comprising using a perforate structure wherein said electromechanical transducer is coupled to said perforate structure.

17. A method according to claim 13 further comprising using a perforate structure wherein said electromechanical transducer is decoupled from said perforate structure.

18. A method according to claim 13 further comprising using an orifice through which said liquid active material is generated, wherein said liquid active material is generated into said atmosphere at a height of about 8 cm from said orifice.

19. A method of distributing a liquid to an atmosphere, said method comprising the steps of:

(a) providing a delivery system for generating droplets comprising:

a liquid reservoir, wherein the liquid reservoir contains a quantity of liquid, an electromechanical transducer in communication with said liquid, a droplet generation element operatively associated with said electromechanical transducer and positioned for contact with said liquid, said droplet generation element defines a plurality of perforations, said perforations having a diameter of about 5 microns to about 7 microns, wherein the delivery system has a deposition of less than about 6 μg and a flow rate of about 30 mg/hr or greater;

(b) activating said electromechanical transducer to distribute said liquid to the atmosphere for a first period, said first period is at least about 50 milliseconds;

(c) deactivating the transducer for a second period, said first period and said second period forming an operating cycle; and (d) repeating said operating cycle at least once.

20. A method of distributing a liquid active material to an atmosphere, said method comprising the steps of:

(a) using a delivery system for generating droplets comprising:

a liquid reservoir, wherein the liquid reservoir contains a quantity of liquid active material, a disc-shaped electromechanical transducer having two opposed faces, a drive electrode disposed on one face and a sense electrode disposed on the opposite face, wherein said disc-shaped electromechanical transducer is in communication with said liquid active material, a droplet generation element operatively associated with said disc-shaped electromechanical transducer and positioned for contact with said liquid active material, said droplet generation element defines a plurality of perforations, said perforations having a diameter of 4.5 microns, wherein the delivery system has a deposition of less than about 6 μg and a flow rate of about 30 mg/hr or greater;

(b) activating said disc-shaped electromechanical transducer to distribute said liquid active material to said atmosphere using said drive electrode and sense electrode; and (c) carrying out said activation for a first period of time of at least about 60 milliseconds.

* * * * *